United States Patent [19]

Zaias

[11] Patent Number: 5,411,741
[45] Date of Patent: May 2, 1995

[54] METHOD AND COMPOSITION FOR SKIN DEPIGMENTATION

[76] Inventor: Nardo Zaias, 9-Island Ave. #2101, Miami Beach, Fla. 33139

[21] Appl. No.: 99,491

[22] Filed: Jul. 29, 1993

[51] Int. Cl.$^6$ .............................................. A61K 9/127
[52] U.S. Cl. .................................... 424/450; 424/62; 424/401
[58] Field of Search .................... 424/450, 401, 62; 428/402.2; 514/356

[56] References Cited

U.S. PATENT DOCUMENTS

| | | | |
|---|---|---|---|
| 3,006,939 | 10/1961 | Pommer et al. | 260/413 |
| 3,746,730 | 7/1973 | Marbet et al. | 260/413 |
| 3,856,934 | 12/1974 | Kligman | 424/62 |
| 3,862,332 | 1/1975 | Barnhart | 424/337 |
| 4,096,240 | 6/1978 | Mathur | 424/59 |
| 4,247,537 | 1/1981 | Lunn et al. | 424/62 |
| 4,466,955 | 8/1984 | Calvo et al. | 424/59 |
| 4,603,146 | 7/1986 | Kligman | 514/559 |
| 4,696,813 | 9/1987 | Higa | 424/59 |
| 4,719,237 | 1/1988 | McCaughan | 514/712 |
| 4,764,505 | 8/1988 | Fujinuma et al. | 514/35 |
| 4,895,727 | 1/1990 | Allen | 424/642 |
| 4,900,757 | 2/1990 | Mao | 514/712 |
| 4,919,921 | 4/1990 | Hatae | 424/62 |
| 4,959,392 | 9/1990 | Robinson | 514/712 |
| 4,959,393 | 9/1990 | Torihara et al. | 514/724 |
| 4,975,467 | 12/1990 | Ku | 514/712 |
| 4,985,465 | 1/1991 | Hendler | 514/712 |
| 5,001,115 | 3/1991 | Sloan | 514/34 |
| 5,034,228 | 7/1991 | Meybeck | 424/401 |
| 5,061,700 | 10/1991 | Dow et al. | 514/169 |
| 5,061,734 | 10/1991 | Mao | 514/712 |
| 5,077,211 | 12/1991 | Yarosh | 435/193 |
| 5,279,834 | 1/1994 | Meybeck | 424/450 |

OTHER PUBLICATIONS

M. M. Wick, V. J. Hearing and H. Rorsman, Biochemistry of Melanization, 251–256 (1993).

Stefan Schmitz, Theresa M. Allen, and Kowichi Jimbow, Polyethelyne-Glycol-Mediated.

Delivery of Liposome-entrapped Pigments into Fibroblasts: Experimental Pigment Cells as Models for Mutator Phenotypes, 6,638–6,645 (Dec. 1, 1992).

"Inhibition of Melanization in Human Melanoma Cells by a Serotonin Uptake Inhibitor", by M. McEwan, P. G. Parsons in J. Investigative Dermatology, 1987, vol. 89, pp. 82–86.

"Regulation of Tyrosinase Expression and Activity in Human Melanoma Cells via Histamine Receptors" by M. T. McEwan and P. G. Parsons in J. Investigative Dermatology, 1991, vol. 97, pp. 868–873.

*Primary Examiner*—Gollamudi S. Kishore
*Attorney, Agent, or Firm*—Shlesinger, Arkwright & Garvey

[57] ABSTRACT

The present invention relates to a composition and method for skin depigmentation comprising the steps of encapsulating an effective amount of a water-soluble melanin inhibiting compound with a liposome, suspending the encapsulated melanin inhibiting compound within a topical vehicle, topically applying to the epidermis of the skin the suspended and encapsulated melanin inhibiting compound whereby the liposomes are transdermally delivered to the basal cell region of the epidermis causing interference with the biochemical synthesis of melanin in situ and subsequent depigmentation of the skin.

7 Claims, No Drawings

# 5,411,741

METHOD AND COMPOSITION FOR SKIN DEPIGMENTATION

FIELD OF THE INVENTION

This invention relates to topically applied skin-lightening cosmetics having melanin synthesis inhibiting activity which promote depigmentation to the human skin and to methods for depigmenting human skin with such cosmetics.

BACKGROUND OF THE INVENTION

The skin of human beings is variously coloured with remarkable individual differences occurring even within members of the same race. The epidermis or upper layer of the skin consists essentially of two major layers. The viable basal layer exists at the bottom of the epidermis in contact with the dermis, while the dead corneal or horny layer exists above the basal layer and extends upward to the surface of the skin.

The colour of human skin is determined by melanin, a biopolymer pigment manufactured by special dendritic cells known as melanocytes residing mostly below or between the basal cells of the epidermis. Melanocytes have been characterized as unicellular "glands" having long, thin, branching, streamer-like dendrites or arms that worm their way between the epidermal cells in their immediate vicinity creating a constellation of epidermal cells around each melanocyte. Melanin is produced in the melanosome region and once produced travels to the dendrites of the melanocyte. Epidermal cells in contact with the melanin-laden dendrites actually phagocytose the tips of the dendrites and transfer the melanin to the surrounding epidermal cells. Once inside the epidermal cells, melanin granules tend to move above the cell nucleus forming a type of shroud over it. This orientation of melanin supports other evidence that it exists to protect cells from damaging ultraviolet rays. In fact, melanin production is stimulated by UV irradiation.

The biochemical process responsible for the production of melanin is caused by the action of an enzyme called tyrosinase which triggers a cascade of biosynthesis. Tyrosinase causes the oxidation of the substrates tyrosine and levodopa to dopaquinone followed by subsequent polymerization of numerous intermediates into melanin. The exact mechanism of melanin biosynthesis is a complex process however the importance of tyrosinase in propelling the overall process is undisputed. M. M. Wick, V. J. Hearing and H. Rorsman, *Biochemistry of Melanization*, pp. 251–256 (19).

Although primary regulation of melanin production is via genetic controls, environmental factors may also play an important role in synthesis. As noted above, exposure to sunlight or other UV radiation can stimulate the melanocytes to produce melanin, hence the so-called "tanning" reaction. Current research suggests that an inhibitor of tyrosinase activity is destroyed by UV radiation thereby allowing for the rapid stimulation of pigment production. Melanin production can also increase in response to hormone fluctuations associated with child bearing or the use of birth-control pills.

Normal pigmentation of the skin surface is uniform, however localized, excessive pigmentation can occur and such colorization is collectively referred to as hyperpigmentation. Hyperpigmentation encompasses a wide array of afflictions all of which are accompanied by increased melanin production. Hyperpigmentation of the human skin may include skin blemishes or disorders including freckles, senile lentigo, liver spots, melasma, brown or age spots, vitiligo, sunburn pigmentation, post-inflammatory hyperpigmentation due to abrasion, burns, wounds, dermatitis, phototosic reaction and other similar small, fixed pigmented lesions. In addition and from a cosmetic standpoint, it may often be desirable to decolorize what is considered normally pigmented skin to increase "fairness" or to blend hyperpigmented regions into that of the surrounding normal skin. Regardless of the type of hyperpigmentation, it is almost always viewed as cosmetically undesirable and often to the point of being psychologically disabling to the patient.

Accordingly, a number of prior art methods and compositions have been developed in an attempt to depigment the skin. Most of these prior art attempts have focused on skin-bleaching compositions such as sodium hypochlorite, hydroquinone, monoethyl ether, ammoniated mercury, zinc peroxide, mercurous chloride and bi-chloride of mercury. These compounds are often disadvantageous due to sensitization, irritation and lack of predictable results. In addition, methods incorporating such compounds are generally ineffective or at the most short lived since they do not address the cause of pigmentation but rather the effects of pigmentation.

To be effective, any treatment must inhibit at the melanocytes either the production of the enzyme tyrosinase since that enzyme is ultimately responsible for conversion of tyrosine into melanin or, the production of intermediates during melanogenesis.

It is known that certain compounds effectively inhibit synthesis of melanin. For example, recent studies have shown that 6-nitroquipazine, a serotonin uptake antagonist, inhibits melanin synthesis without affecting tyrosinase activity. See "Inhibition of Melanization in Human Melanoma Cells by a Serotonin Uptake Inhibitor" by M. McEwan, P. G. Parsons in J. INVESTIGATIVE DERMATOLOGY, 1987, Vol. 89, pp. 82–86.

Other studies have shown that tyrosinase activity and consequently melanin production can be decreased and eventually halted by various histamine agonists. See "Regulation of Tyrosinase Expression and Activity in Human Melanoma Cells via Histamine Receptors" by M. T. McEwan and P. G. Parsons in J. INVESTIGATIVE DERMATOLOGY, 1991, Vol. 97, pp. 868–873.

Although various prior art depigmentation compositions have included melanin synthesis inhibiting compounds, they are for the most part ineffective since they don't truly inhibit the activity of tyrosinase or sufficiently interfere with melanin biosynthesis. For example, in U.S. Pat. No. 4,919,291 (Hatae) kojic acid and its esters has been combined with Vitamin C in a topical composition for use as a depigmentation cream. Kojic acid is known to inhibit synthesis of melanin. U.S. Pat. No. 3,856,934 (Kligman) discloses a topical composition combining retinoic acid and corticosteriod to synergistically create a melanin inhibiting topical composition. U.S. Pat. No. 4,096,240 (Mathur) discloses combining Niacinamide with a UV absorbing sunscreen for use in a topical composition to "retard" melanin dispersion or distribution into the epidermis. Although each of above noted compositions include melanin inhibiting ingredients in various topical oils, lotions or emulsions, none of the compositions have been found to be effective since the water-solubility of the melanin inhibiting compound prevents delivery into the basal cell region of the epidermis. These penetrating lotions and oils and active ingredients are invariably adsorbed into the upper layer of the epidermis and dispersed well before they can reach the basal cell layer to interfere with melanin production.

In addition, many carriers can cause an adverse reaction in the user. For example, while dimethyl sulfoxide (DMSO) has found wide use as a penetrant carrier it can also cause extreme skin irritation, redness, itching and scaling. Water soluble organic or inorganic zinc salts have also been proposed as pharmaceutical vehicles for enhancing penetration and retention of drugs into the skin. These carriers have likewise been met with mixed success since they are not inert and often interfere with the action of the active ingredient or cause allergic reactions to the patient. Further, none of the prior art penetrant carriers deliver the active ingredient to the basal cell region intact. The water soluble characteristics of both the carriers and active ingredients results in premature dispersion within the skin well before the melanocyte region. Thus, despite the development of various melanin inhibiting compounds, prior art methods and compositions only provide short term relief with relatively large doses being required to compensate for excessive adsorption into the surrounding epidermal layers.

It is known to administer DNA repair enzymes in an active form to living cells in situ via topical compositions. In U.S. Pat. No. 5,077,211 (Yarosh) enzymes are first encapsulated within liposomes and the liposomes are subsequently suspended in a topical vehicle. The liposomes provide a non-toxic means for encapsulation and can be further modified to bind to specific subpopulations of cells. Liposomes have also been previously used to encapsulate melanin for introduction into non-pigmented human fibroblast. See "Polyethylene-Glycol-mediated Delivery of Liposome-entrapped Pigments into FibroblaSts: Experimental Pigment Cells as Models for Mutator Phenotypes" by S. Schmitz, T. M. Allen and K. Jimbow in CANCER RESEARCH, 1992, Vol. 52, pp. 6638–6645.

A need has therefore existed within the art for a method and composition of skin depigmentation which possesses true melanin synthesis inhibiting activity and one which can be effectively delivered through the skin via a topical composition for eventual adsorption into the basal cell region of the skin thereby promoting interference of melanin production.

OBJECTS AND SUMMARY OF THE INVENTION

It is therefore an object of the present invention to provide a method for skin depigmentation which interferes with the normal biosynthesis of melanin at the cellular level.

Another object of the present invention is to provide a cosmetic composition for skin depigmentation which is readily adsorbed into the basal region of the epidermis for targeted interference of melanin production at the melanocyte near the basal cell region of the epidermis.

Still a further object of the present invention is to provide a method and composition for skin depigmentation which is highly effective in extremely low concentrations.

Still a further object of the present invention is to provide a method and composition which has long lasting effects, is a low irritant to the skin, non-toxic to the surrounding tissue and is highly adsorbable and biocompatible.

A further object of the invention is to provide a method of depigmentation therapy which produces marked improvement in skin tone and which has long lasting results.

Yet another object of the present invention is to provide a method of depigmentation which delivers the active ingredient to the target cells with little or no dilution.

A still further object of the present invention is to provide a single composition containing plural melanin synthesis inhibiting compounds having enhanced skin depigmentation.

Yet another object of the present invention is to provide a method for encapsulation of melanin inhibiting compounds within a liposome.

These and other objects are achieved by a method of depigmentation of the skin comprising the steps of encapsulating an effective amount of a water-soluble melanin inhibiting compound within a liposome. Suspending the encapsulated melanin inhibiting compound within a topical vehicle. Topically applying to the epidermis of the skin the suspended and encapsulated melanin inhibiting compound whereby the liposomes are transdermally delivered to the basal cell region of the epidermis causing interference with the biochemical synthesis of melanin in situ.

Additional objects, advantages and features of the present invention will become apparent from a consideration of the following specification.

DETAILED DESCRIPTION OF THE PREFERRED EMBODIMENT

The present invention provides a method and means for administering melanin inhibiting compounds in situ to living cells via topical application to the epidermis of the skin. In particular, melanin inhibiting compounds are encapsulated in liposomes to form cosmetic preparations suitable for topical administration to the living cells of human skin. When delivered to human melanocytes at the basal cell region of the epidermis, the melanin inhibiting compound will enter the melanosomes and cause interference with melanin production and the resultant gradual depigmentation of the surface skin.

The delivery system according to the present invention has the advantage of providing melanin inhibiting compounds only within the liposomes so as to protect the integrity of the melanin inhibiting active ingredients until it reaches the basal cell region of the epidermis. Thus, the melanin inhibiting compounds according to the present invention are delivered intact and in their entirety to the target cells. The liposome membranes according to the present invention can be made to bind to specific sub-populations of the basal cell region thereby increasing efficiency and/or specificity of melanin-inhibiting compound delivery.

Liposomes are microscopic spherical membrane-enclosed vesicles or sacs (20–30mm in diameter) made artificially in the laboratory by a variety of methods. The primary restrictions according to the present invention are that the liposomes should not be toxic to the living cells and that they should deliver the contents into the interior of the cells being treated.

The liposomes according to the present invention may be of various size and may comprise either one or several membrane layers separating the internal and external compartments. The most important element in liposome structures is that a sufficient amount of melanin-inhibiting compound is sequestered so that only one or a few liposomes are required to enter each melanosome for delivery of the melanin inhibiting active ingredients and further that the liposome be resistant to destruction as it travels from the surface of the skin down to the basal cell region of the epidermis. Liposome structures according to the present invention include small unilamellar vesicles (less than 250 angstroms in diameter), large unilamellar vesicles (greater than 500 angstroms in diameter) and multilamellar vesicles depending upon the type of melanin inhibiting compounds sought to be encapsulated. In the present invention small unilamellar vesicles are preferred since the melanin inhibiting compound according to the present invention is only required in extremely low concentrations in order to inhibit melanin production.

The liposomes according to the present invention may be made from natural and synthetic phospholipids, glycolipids and other lipids and lipid congeners; cholesterol, cholesterol derivatives and other cholesterol congeners; charged species which impart a net charge to the membrane; reactive species which can react after liposome formation to link additional molecules to the liposome membrane; and other lipid soluble compounds which have chemical or biological activities.

The liposomes of the present invention are prepared by combining a phospholipid component with an aqueous component containing the selected melanin inhibiting compound under conditions which will result in vesicle formation. The phospholipid concentration must be sufficient to form lamellar structures, and the aqueous component must be compatible with the melanin inhibiting compound. Methods for combining the phospholipid and the aqueous components so that vesicles will form include: drying the phospholipids onto glass and then dispersing them in the aqueous components; injecting phospholipids dissolved in a vaporizing or non-vaporizing organic solvent into the aqueous component which has previously been heated; and dissolving phospholipids in the aqueous base with detergents and then removing the detergent by dialysis. The lipoproteins can be produced from the foregoing mixtures either by sonication or by dispersing the mixture through either small bore tubing or through the small orifice of a French Press. The methods for producing the liposomes as set forth in U.S. Pat. No. 5,077,211 (Yarosh) are incorporated herein by reference.

It is within the scope of the present invention to use other methods for encapsulating the melanin inhibiting compound within a liposome. A specific example of producing the liposomes would include the following. A lipid mixture as set forth above is dissolved in an organic solvent and dried to a thin film in a glass vessel. The selected melanin inhibiting compound is purified and added to the vessel at high concentrations in an aqueous buffer to rehydrate the lipid. The mixture is then agitated by vortexing and sonicated to form liposomes. The liposome spheres containing the encapsulated melanin inhibiting compound are then separated from the unincorporated melanin inhibiting compound by centrifugation or gel filtration.

The liposome encapsulated melanin inhibiting compounds are then administered to the melanosomes at the basal cell region of the epidermis by topical application to the skin. This administration to human requires that the liposomes be pyrogen-free and sterile. To eliminate pyrogens, pyrogen-free raw materials, including all chemicals as well as the melanin-inhibiting compounds and water are used to form the liposomes. Sterilization can be performed by filtration of the liposomes through a 0.2 micron filter. A physiologically effective concentration of liposomes is then suspended in a buffered polymeric glycol gel carrier for even application to the skin. In general, the gel carrier should not include nonionic detergents which can disrupt the liposome membranes. Other similar vehicles can also be used to topically administer the liposomes. The concentration of the melanin-inhibiting compound in the final preparation can vary over a wide range, a typical concentration according to the present invention is in the order of 0.001% by weight to about 3.0% by weight.

A general discussion of liposomes and liposome technology can be found in an article entitled "Liposomes" by Marc J. Ostro, published in SCIENTIFIC AMERICAN, January 1987, Vol. 256, pp. 102–111 and in a three volume work entitled Liposome Technol by G. Gregoriadis, 1984, published by CRC Press, Boca Raton, Fla. The pertinent portions of each of these references are incorporated herein by reference.

The melanin inhibiting active ingredients for use according to the present invention include a variety of water soluble compounds that have known melanin inhibiting activity by either inhibiting the production of tyrosinase or inhibiting the intermediates produced during melanin production. These compounds include antioxidant free radical traps. Examples of such compounds, which may collectively be referred to herein as "antioxidants" include the following: the drug probucol and its derivatives which is obtainable under the name Lorelco ® (Merrell Pharmaceutical, Inc.). Butylated hydroxytoluene (BHT) and derivatives thereof, said derivatives comprising conjugates of from about one to about four modified BHT moieties. Examples of such compounds include Ethanox ® compounds which are commercially available from the Ethyl Corporation (Baton Rouge, La.).

Other significant groups of melanin inhibiting compounds include those which inhibit cyclic AMP. Cyclic AMP is a derivative of ATP that is widespread in animal cells as an intermediate messenger in a great variety of biochemical reactions induced by hormones. Since cyclic AMP has been found to be the ultimate activator of enzymes in a variety of reactions including melanogenesis, "anti-cyclic AMP" compounds are known to inhibit melanogenesis and are therefore within the scope of the present invention. For example, Niacinamide (3-pyridinecarboxamide) has been found to be a suitable anti-cyclic AMP compound according to the present invention and when used in an amount between about 1 to about 10% by weight of the total topical composition inhibits melanin production at the melanocyte.

Another group of applicable compound within the scope of the present invention include those which inhibit melanogenesis through the inhibition of tyrosinase. These compounds include "histamine agonists" such as Nordimaprit and Dimaprit (Smith, Kline and French Research Ltd., Hertfordshire, U.K.). Still other compounds within the scope of the present invention include "seratonin uptake inhibitors" compounds which interfere with melanogenesis by inhibiting dopa rather tyrosinase activity. Representative "seratonin uptake inhibitors" within the scope of the present invention include DU 24565 (6-nitroquipazine) available from Duphar Laboratories Ltd., South Hampton, UK. Yet another melanin inhibiting compound within the scope of the present invention includes various "pituitary-ovarian axis suppressors" such as Danocrine ® (danazol) a synthetic steroid derived from ethisterone and available through Sterling Drug Company.

Secondary additives to the present invention include various forms of Vitamin E such as α-tocopherol, β-tocopherol, γ-tocopherol all of which function as an antioxidant. Yet another secondary additive includes a Vitamin C, a known reducing agent.

The above noted active ingredient compounds of the present invention may be administered within a single topical carrier in various efficacious amounts. The compounds may be first encapsulated within the liposome separately and then intermixed as a formulated blend into a polyethylene glycol base. In a preferred embodiment, the active ingredient concentration range is about 0.001% to 3% by weight although higher concentrations and lower concentrations may be used for varying types of skins. Although a polyethylene glycol having a weight between about 200 to about 3000 is preferred, any emollient or lubricating vehicle having similar properties to polyethylene glycol and which will help hydrate the skin are preferred.

The extent or length of treatment according to the present invention may best be described as persistent with a "ladder-like" phenomenon of improvement over six to eight week periods, each successive period of which results in an improvement over the prior period. Eventually, the skin will be completely depigmentated and application according to the present method can be stopped without recurrence of pigmentation. That is, compared to the short term prior art treatments of depigmentation formulas the treatment according to the present invention is applied over the long term for a slow and successive improvement within the patients skin. Once a stabilization of skin colorization has been obtained, the frequency of application may be reduced to one or two times a week as a maintenance dose to continue to inhibit melanogenesis within the epidermis.

The invention will be illustrated in more detail by reference to the following specific, nonlimiting example:

EXPERIMENTAL EXAMPLE 1

A group of 240 patients were arranged, each of which showed various hyperpigmentory characteristics such as melasma, freckles and post inflammatory hyperpigmentation all of which included brownish or brownish-black patches upon their skin. The patients were divided into two separate groups of 120 with the first group having applied to their skin two times daily the liposome encapsulated anti-cyclic AMP compound nicotinamide having a concentration of 1% by weight in a polyethylene glycol base. The second group was treated via the application of a conventional UV screen cream and moisturizer (aloe vera). Clinical assessments were made after the third week.

Beneficial results were obtained after the third week ranging from a good improvement (60 to 80% clear up) with some brownish-black pigmentation remaining to excellent (80 to 100% of the skin was cleared) with only some brownish spots remaining. After a twelve week period 89% of all the results within the first group were characterized between good and excellent. Throughout the treatment neither peeling nor an increase of pigmentation within the first group was found. Good to excellent results were found in the second group by the eighth week and after twelve weeks 18% of the results in the second group were between good to excellent.

A series of follow up examinations over 32 months was made on the patients who continued applying the medication according to the present invention. The results found that after a relatively significantly initial improvement, the patient experiences a plateau in improvement after six to eight weeks with an additional jump in further improvement over the next six to eight week period. Although continued maintenance therapy was required in some patients to prevent relapse, the overall beneficial effects included no less than a 60% improvement in any patient receiving treatment according to the present invention.

While this invention has been described as having a preferred design, it is understood that it is capable of further modifications, uses and/or adaptions of the invention following in general the principle of the invention including such departures form the present disclosure as come within the known or customary practice in the art to which the invention pertains, and as may be applied to the central features set forth and fall within the scope of the invention and the limits of the appended claims.

I claim:
1. A method of depigmentation of skin comprising the steps of:
   a) encapsulating an effective amount of a water-soluble melanin inhibiting compound within a liposome, said melanin inhibiting compound is 3-pyridinecarboxamide;
   b) suspending the encapsulated melanin inhibiting compound in a topical vehicle; and
   c) typically applying to the epidermis of the skin the suspended and encapsulated melanin inhibiting compound whereby the liposomes are transdermally delivered through the basal cell region of the epidermis to cause interference with the biochemical synthesis of melanin in situ and subsequent depigmentation of the skin.
2. The method of claim 1 and wherein:
   a) said melanin inhibiting compound may be encapsulated singly or in combination with additional melanin inhibiting compounds.
3. The method of claim 1 and wherein:
   a) said effective amount of melanin inhibiting compound is at least 0.001% by weight to about 3% by weight of said suspended and encapsulated melanin inhibiting compound.
4. The method of claim 1 and wherein:
   a) said vehicle is a cosmetically acceptable vehicle.
5. The method of claim 4 and wherein:
   a) said topical vehicle comprises a cream, ointment, emulsion or lotion.
6. The method of claim 4 and wherein:
   a) said cosmetically acceptable topical vehicle is selected from the group consisting of beeswax, cetyl alcohol, stearic acid, glycerins, propylene glycol monostearate and polyoxyethylene cetyl ether.
7. The method of claim 1 and wherein;
   a) said topical vehicle includes vitamin C and vitamin E.

* * * * *